United States Patent
Hwang et al.

(10) Patent No.: US 6,617,028 B1
(45) Date of Patent: *Sep. 9, 2003

(54) PHOSPHORUS AND NITROGEN CONTAINING RESIN HARDENER AND A FLAME RETARDING RESIN COMPOSITION CONTAINING SAID HARDENER

(75) Inventors: Kuen Yuan Hwang, Hsinchu (TW); Hong Hsing Chen, Hsinchu (TW); An Pang Tu, Hsinchu (TW)

(73) Assignee: Chang Chun Plastics Co., Ltd., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 09/619,102

(22) Filed: Jul. 19, 2000

(30) Foreign Application Priority Data

Nov. 5, 1999 (TW) ........................................ 88119300 A

(51) Int. Cl.$^7$ ........................ B32B 27/38; C07F 9/6571; C08G 59/50
(52) U.S. Cl. ....................... 428/413; 252/609; 428/417; 428/921; 523/435; 525/526; 558/77; 528/108; 528/118
(58) Field of Search ................ 528/108, 118; 523/435; 544/194, 195; 252/609; 428/413, 417; 525/526; 558/77

(56) References Cited

U.S. PATENT DOCUMENTS

| | | | | |
|---|---|---|---|---|
| 3,296,265 A | * | 1/1967 | Garner | 252/609 X |
| 3,755,323 A | * | 8/1973 | Weil et al. | 528/108 X |
| 3,759,914 A | * | 9/1973 | Simms et al. | 528/118 X |
| 4,973,631 A | | 11/1990 | McGrath et al. | 525/534 |
| 5,086,156 A | | 2/1992 | McGrath et al. | 528/108 |
| 5,112,926 A | * | 5/1992 | Lee et al. | 528/118 X |
| 5,284,604 A | * | 2/1994 | Nishibori et al. | 523/435 X |
| 5,376,453 A | | 12/1994 | Von Gentzkow et al. | 428/415 |
| 5,458,978 A | | 10/1995 | Böttcher et al. | 428/413 |
| 5,534,573 A | * | 7/1996 | Leake | 544/195 X |
| 5,821,317 A | * | 10/1998 | Buser et al. | 528/118 X |
| 5,844,028 A | * | 12/1998 | Paulik | 558/77 X |
| 6,432,539 B1 | * | 8/2002 | Hwang et al. | 428/413 |

* cited by examiner

Primary Examiner—Richard D. Lovering
(74) Attorney, Agent, or Firm—Michael Best & Friedrich, LLP; Teresa J. Welch; Jeffrey D. Peterson

(57) ABSTRACT

The present invention discloses a phosphorus- and nitrogen-containing resin hardener, which has a structure represented by the following formula:

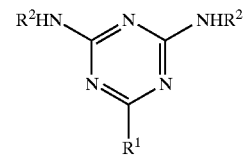

wherein $R^2$ represents a hydrogen atom or a group represented by the following formula:

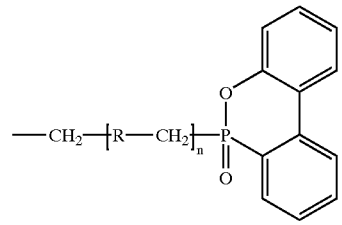

wherein n is an integer of from 0 to 20, and R represents phenylene, naphthylene or a group represented by the following formula:

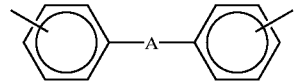

wherein A represents —O—, —S—, —SO$_2$—, —CO—, —CH$_2$—, —C(CH$_3$)$_2$— or a group represented by the following formula:

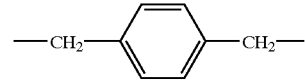

provided that at least one $R^2$ is not a hydrogen atom; and $R^1$ represents NHR$^2$, C$_{1-6}$alkyl or phenyl; in the above groups represented by R and A, the aromatic group can be substituted by one or more substituents selected from the group consisting of hydroxy, amino, carboxy and C$_{1-6}$alkyl. The present invention also discloses a flame retarding composition containing said hardener.

14 Claims, No Drawings

PHOSPHORUS AND NITROGEN CONTAINING RESIN HARDENER AND A FLAME RETARDING RESIN COMPOSITION CONTAINING SAID HARDENER

FIELD OF THE INVENTION

The present invention discloses a phosphorus- and nitrogen-containing resin hardener, and a flame retarding resin composition containing said hardener.

While the flame retarding resin composition of the present invention does not contain halogen or diantimony trioxide, it has the flame retardant property of the UL94V-0 standard and high heat resistance. Therefore, it is useful in making prepregs, composites, laminates, printed circuit boards, substrates for build-ups of resin coated copper (RCC), epoxy molding compounds and the like.

BACKGROUND OF THE INVENTION

Because of easy processing, high safety, excellent mechanical and chemical properties, the composite material, especially the epoxy resin material, has been widely used in various fields such as coating, electrical insulating, construction building materials, adhesives and laminated products. Since epoxy resins have strong adhesion to reinforcement materials such as glass-fiber fabric, no volatiles while hardening, and small shrinkage in molding, a laminated plate produced by such resins has the advantages of broad range usability, good mechanical strength, good electrical insulation characteristics and excellent resistance to chemicals, etc. In addition, this laminate material is highly reliable. Thus, the laminated plate obtained has been massively applied to electrical and electronic products.

However, since the demand for finer circuits and higher density of the printed circuit board is increasing day by day, the laminated plate has been required to possess better electrical, mechanical, and heat resistant processing properties. Widely used at present, the glass transition temperature (Tg) after hardening of FR4 laminated plate is generally about 130° C. Thus, when the temperature of cutting and drilling rises over 200° C. during the process of producing the printed circuit board and over 270° C. during the welding process, the plate breaks or cracks easily. Therefore, various laminate materials which evince higher heat stability and higher glass transition temperature are constantly being developed. In addition, another important requirement for the laminated plate to possess is flame retarding properties. The flame retarding property of a printed circuit board is absolutely necessary, because safety of life and property is involved as the printed circuit board is frequently used in airplanes, automobiles and all forms of public transportation.

In order to render a flame retarding property to the laminate material, substances that separate the flame and decrease burning should be introduced. For laminated plates of epoxy resin/glass-fiber (or organic fiber) systems, halogen-containing compounds, especially bromine-containing epoxy resins and hardeners, are used, in combination with flame retarding auxiliaries such as diantimony trioxide, etc., so that the strict flame retarding standards (as UL94V-0 level) in the laminated plates can be achieved. Generally, epoxy resins reach the level of UL94V-0 standard, only when the bromine content is as high as 17 to 21%, and combines with diantimony trioxide or other flame retardants. However, the use of high bromine content epoxy resin or diantimony trioxide will doubtlessly endanger human life.

In the first place, diantimony trioxide has been considered as a carcinogen. On the other hand, bromine generates not only erosive free radicals and hydrogen bromide, aromatic compounds with high bromine content also produce toxic brominated furans and brominated dioxines during the burning process. These seriously affected the health of the human body and the environment. Thus, at the present time, it becomes most urgent to find a novel flame retarding material and flame retarding method, in order to improve the pollution and environmental protection problems resulting from using laminated plates made by the brominated epoxy resin. This requirement is especially demanding, since large amounts of FR4 type of epoxy glass fiber laminate are used.

Phosphorus compounds have been extensively studied and applied to the new generation of flame retardants designed for environmental protection. For example, red phosphorus- or phosphorus-containing organic compounds (such as triphenyl phosphonate, triphenylmethyl phosphonate, phosphoric acid and the like) are used as flame retardants to replace halogen compounds to improve the burning properties of the high molecular material or hardened-type resins. However, when these kinds of compounds are added directly to the resin, not only are massive amounts needed because of the limitation of the flame retarding efficiency of these compounds, but also the characteristics of the resin material such as electrical properties are adversely affected because of their low molecular weight and high migration property, resulting in difficulties in practice.

Recently, with the concept of reaction type flame retardant, in combination with considering environmental protection and safety, phospho-epoxy resins have been used to replace bromo-epoxy resins to obtain a flame retarding laminated plate. For example, U.S. Pat. No. 5,376,453 has disclosed a laminated plate made from epoxy-containing phosphates in combination with nitrogen-containing cyclic hardeners. However, various phosphate epoxides have been added in order to make up for the insufficient phosphorus content and to reach the hardly achievable UL94V-0 standard. In U.S. Pat. No. 5,458,978, where epoxy phosphates in combination with nitrogen-containing epoxy resins and metal complexes are used as hardeners, the glass transition temperature of the products is about 175° C., and the flame retarding properties only reach the edge of UL94V-0(42 seconds, as opposed to the critical value of 50 seconds). U.S. Pat. No. 4,973,631 and U.S. Pat. No. 5,086,156 use tri (hydrocarbyl)phosphine oxide derivatives with active hydrogen substituents (such as an amino group) alone, or in combination with other amino hardeners, to harden epoxy resins. However, the disadvantage of using hardeners to introduce phosphorus into resins is low phosphorus content. Besides, the flame retardant effects are not actually measured in these two patents.

The present inventors aim to correct the defects of the conventional techniques, promote the electrical and mechanical properties of the resin composition while decreasing the cost, and have made extensive studies to complete this invention.

DETAILED DESCRIPTION OF THE INVENTION

The present invention discloses a phosphorus- and nitrogen-containing resin hardener, which has a structure represented by the following formula:

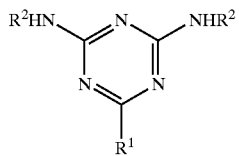

wherein $R^2$ represents a hydrogen atom or a group represented by the following formula:

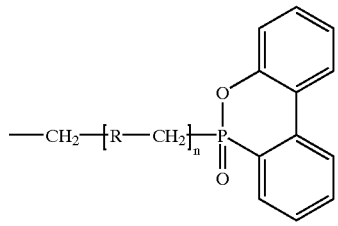

wherein n is an integer of from 0 to 20, and
R represents phenylene, naphthylene or a group represented by the following formula:

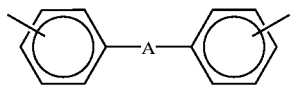

wherein A represents —O—, —S—, —SO$_2$—, —CO—, —CH$_2$—, —C(CH$_3$)$_2$— or a group represented by the following formula:

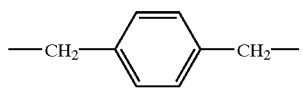

provided that at least one $R^2$ is not a hydrogen atom; and $R^1$ represents $NHR^2$, $C_{1-6}$alkyl or phenyl.

In the above groups represented by R and A, the aromatic group can be substituted by one or more substituents selected from the group consisting of hydroxy, amino, carboxy and $C_{1-6}$alkyl.

The present invention also relates to a flame retarding resin composition, which comprises (A) an epoxy resin, (B) the above-mentioned phosphorus- and nitrogen-containing resin hardener and (C) a hardening prompter.

The epoxy resin contained in the flame retarding resin composition of the present invention may be any epoxy resin, and is exemplified by glycidyl ethers of bisphenols, glycidyl ethers of biphenols, glycidyl ethers of dihydroxybenzenes, glycidyl ethers of nitrogen-containing hetero rings, glycidyl ethers of dihydroxynaphthalene, polyglycidyl ethers of phenolics, polyglycidyl ethers of polyhydric phenols and the like.

Examples of glycidyl ethers of bisphenols include bisphenol A glycidyl ether, bisphenol F glycidyl ether, bisphenol AD glycidyl ether, bisphenol S glycidyl ether, tetramethyl bisphenol A glycidyl ether, tetramethyl bisphenol F glycidyl ether, tetramethyl bisphenol AD glycidyl ether, tetramethyl bisphenol S glycidyl ether and the like.

Examples of glycidyl ethers of biphenols include, for example, 4,4'-biphenol glycidyl ether, 3,3'-dimethyl-4,4'-biphenol glycidyl ether, 3,3',5,5'-tetramethyl-4,4'-biphenol glycidyl ether and the like.

Examples of glycidyl ethers of dihydroxybenzenes include, for example, resorcinol glycidyl ether, quinol glycidyl ether, isobutylquinol glycidyl ether and the like.

Examples of polyglycidyl ethers of phenolics include, for example, phenolic polyglycidyl ether, cresol phenolic polyglycidyl ether, bisphenol A phenolic polyglycidyl ether and the like.

Examples of polyglycidyl ethers of polyhydric phenols include, for example, tris(4-hydroxyphenyl)methane polyglycidyl ether, tris(4-hydroxyphenyl)ethane polyglycidyl ether, tris(4-hydroxyphenyl)propane polyglycidyl ether, tris(4-hydroxyphenyl)butane polyglycidyl ether, tris(3-methyl4-hydroxyphenyl)methane polyglycidyl ether, tris(3,5-dimethyl-4-hydroxyphenyl)methane polyglycidyl ether, tetrakis(4-hydroxyphenyl)ethane polyglycidyl ether, tetrakis(3,5-dimethyl-4-hydroxyphenyl)ethane polyglycidyl ether, bicyclopentene-phenolic polyglycidyl ether and the like.

Examples of glycidyl ethers of nitrogen-containing hetero rings include, for example, triglycidyl ether of isocyanuric acid ester, triglycidyl ether of cyanuric acid ester and the like.

Examples, of glycidyl ethers of dihydroxynaphthalenes include, for example, 1,6-dihydroxynaphthalene diglycidyl ether, 2,6-dihydroxynaphthalene diglycidyl ether and the like.

These epoxy resins can be used alone or two or more of them can be mixed.

Among them, the preferred examples are bisphenol A glycidyl ether, phenolic polyglycidyl ether, tris(4-hydroxyphenyl)methane polyglycidyl ether, bicyclopentene-phenolic polyglycidyl ether, tetrakis(4-hydroxyphenyl)ethane polyglycidyl ether, and mixtures thereof.

The preferred phosphorus- and nitrogen-containing resin hardener contained in the flame retarding resin composition of the present invention are compounds of the following formula:

A-1

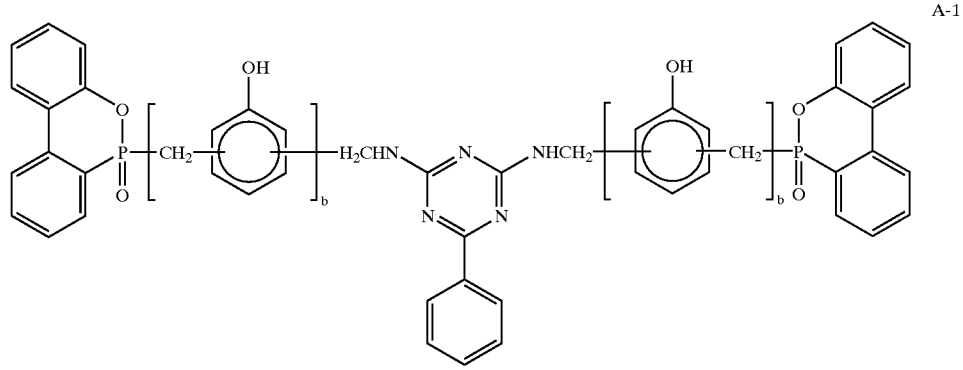

wherein b is an integer of from 0 to 20.

In addition to the phosphorus- and nitrogen-containing resin hardener of the present invention, the flame retarding resin composition of the present invention may also contain other hardeners not containing halogen. Such hardeners not containing halogen include amines, bisphenolic resin, dihydroxybenzenes, polyhydric phenolic resin, phenolics and the like.

Examples of suitable amines include, for example, dicyanodiamide, diaminodiphenylmethane and the like.

Suitable bisphenolic resin includes compounds represented by HO—Ph—X—Ph—OH (wherein Ph represents phenylene and X represents —$CH_2$—, —$C(CH_3)_2$—, —O—, —S—, —CO—, —$SO_2$—), for example, bisphenol A, bisphenol F, bisphenol AD, bisphenol S, tetramethyl bisphenol A, tetramethyl bisphenol F, tetramethyl bisphenol AD, tetramethyl bisphenol S, 4,4'-biphenol, 3,3'-diethyl-4,4'-biphenol, 3,3',5,5'-tetramethyl-4,4'-biphenol and the like.

Examples of suitable dihydroxybenzenes include, for example, resorcinol, quinol, isobutylquinol and the like.

Examples of suitable polyhydric phenolic resin include, for example, tris(4-hydroxyphenyl)methane, tris(4-hydroxyphenyl)ethane, tris(4-hydroxyphenyl)propane, tris(4-hydroxyphenyl)butane, tris(3-methyl-4-hydroxyphenyl)methane, tris(3,5-dimethyl-4-hydroxyphenyl)methane, tetrakis(4-hydroxyphenyl)ethane, tetrakis(3,5-dimethyl-4-hydroxyphenyl)ethane and the like.

Examples of suitable phenolics include, for example, phenol-formaldehyde condensate, cresol phenolic condensate, bisphenol A phenolic condensate, bicyclohexene-phenolic condensate and the like.

In the flame retarding resin composition of the present invention, the added amount of the hardeners depends on the equivalent weight of the reactive hydrogen m the hardeners and the epoxy equivalent weight of the epoxy resin. Generally, the preferable ratio is 20 to 140%, the more preferable ratio is 40 to 95%, and the most preferable ratio is 50 to 95%, of the equivalent weight of the reactive hydrogen in the hardeners, when the epoxy equivalent weight of the epoxy resin is taken as 100%.

When other hardeners not containing halogen are used in the flame retarding resin composition of the present invention, the ratio of the phosphorus- and nitrogen-containing resin hardener of the present invention to said hardener not containing halogen is from 5:95 to 100:0, preferably firm 20:80 to 100:0, and more preferably from 25:75 to 100:0. If the content of the phosphorus- and nitrogen-containing resin hardener of the present invention is too low, insufficient flame retarding property and insufficient heat resistance will easily result.

The hardening promoters employed in the flame retarding resin composition of the present invention are, for example, tertiary amines, tertiary phosphines, quaternay ammonium salts, quaternary phosphonium salts, boric trifluoride complexes, lithium compounds, imidazole compounds and the mixture thereof.

The tertiary amines include, for example, triethylamine, tributylamine, dimethylethanolamine, dimethylaniline, tris(N,N,-dimethylaminomethyl)phenol, N,N-dimethylaminocresol and the like.

The tertiary phosphines include, for example, triphenylphosphine.

The quaternary ammonium salts include, for example, tetramethylammonium chloride, tetramethylammonium bromide, tetramethylammonium iodide, triethylbenzylammonium chloride, triethylbenzylammonium bromide, triethylbenzylammomonium iodide and the like.

The quaternary phosphonium salts include, for example, tetrabutylphosphonium chloride, tetrabutylphosphonium bromide, tetrabutylphosphonium iodide, tetrabutylphosphonium acetate complex, tetraphenylphosphonium chloride, tetraphenylphosphonium bromide, tetraphenylphosphonium iodide, ethyltriphenylphosphonium chloride, ethyltriphenylphosphonium bromide, ethyltriphenylphosphonium iodide, ethyltriphenylphosphonium acetate complex, ethyltriphenylphosphonium phosphate complex, propyltriphenylphosphonium chloride, propyltriphenylphosphonium bromide, propyltriphenylphosphonium iodide, butyltriphenylphosphonium chloride, butyltriphenylphosphonium bromide, and butyltriphenylphosphonium iodide and the like.

The imidazole compounds include, for example, 2-methylimidazole, 2-phenylimidazole, 2-ethyl-4-methylimidazole and the like.

These hardening promoters can be used alone, or two or more of them can be mixed.

The preferred hardening promoters are tertiary ammnes and imidazole compounds, especially dimethylaniline, 2-methylimidazole, 2-phenylimidazole and 2-ethyl-4-methylimidazole.

The suitable amount of hardening promoters used is from 50 to 50,000 ppm, preferably from 100 to 30,000 ppm, more preferably from 200 to 10,000 ppm, and most preferably from 500 to 2,000 ppm, based on the total weight of the flame retarding resin composition of the present invention. If the amount of the hardening promoter exceeds 50,000 ppm, the reaction time can be shortened, but by-products and adverse effects of electrical properties, moisture resistance and water-absorbency on subsequent application such as circuit board laminate will be produced. If the amount used is too low, the reaction will be too slow and lack efficiency.

The viscosity of the flame retarding resin composition can be adjusted by the addition of a solvent, when it is to be formulated into a vanish. The solvents which can be used are, for example, aromatic hydrocarbons, ketones, protic solvents, ethers, esters and the like.

Suitable aromatic hydrocarbons include, for example, toluene and xylene.

Suitable ketones include, for example, acetone, methyl ethyl ketone and methyl isobutyl ketone.

Suitable protic solvents include, for example, N,N-dimethyl formamide, N,N-diethyl formamide and dimethylsulfoxide.

Suitable ethers include, for example, ediylene glycol monomethyl ether and propylene glycol monomethyl ether.

Suitable esters include, for example, ethyl acetate, ethyl isopropanate and propylene glycol monomethyl ether ethyl ester.

Usually, the viscosity is adjusted to the range of 20 to 500 cps/25° C.

Conventional additives or modifiers such as heat stabilize, light stabilizers, UV absorbents and plasticizers can be added in the flame retarding resin composition of the present invention, depending on its ultimate usage.

The flame retarding resin composition of the present invention can be manufactured by conventional methods into laminated entities which comprise copper foil, fiber supports and the resin composition of the present invention.

The flame retarding resin composition of the present invention can be formulated into a varnish; it is then impregnated with fibrous material such as organic or inorganic fibrous material, for example, glass fiber, metallic fiber, carbonaceous fiber, aramid fiber, boron, cellulose and the like. The impregnated fibrous material is then dried by heating, and a dried prepreg is obtained. The dried prepreg can further be formed into composite laminated plates, or it can be used alone in a binding layer of other prepregs. As well, a copper foil is placed on one surface or both surfaces of a prepreg or a combination of more prepregs, and is then pressurized and heated to obtain a laminated plate. The laminated plate composite thus obtained is by far superior to the standards of the present products in the market in respect to size stability, resistance to chemicals, resistance to corrosion, moisture absorption and electrical properties, and is suitable for producing electrical products for electronics, space and transport, and for manufacturing printed circuit boards and multi-layered circuit boards.

As well, the flame retarding resin composition of the present invention can be formulated into a varnish, which is then coated on a copper foil. The coated copper foil is dried by heating, and a dried resin coated copper (RCC) is obtained. The obtained RCC, which can be stored at room temperature for several months, has excellent storage stability. This RCC can further be formed into composite laminated plates, or it can be used alone in a binding layer of other prepregs. As well, layer by layer of RCCs can be built up on one surface or both surfaces of a RCC or a combination of more RCCs. The laminated plate composite thus obtained is by far superior to the standards of the present products in the market in respect to size stability, resistance to chemicals, resistance to corrosion, moisture absorption and electrical properties, and is suitable in manufacturing multi-layered printed circuit boards used in electronics, space and transport.

Suitable temperature of the hardening reaction in the flame retarding resin composition of the present invention is from 20° C. to 350° C., preferably from 50° C. to 300° C., more preferably from 100° C. to 250° C., and most preferably from 120° C. to 220° C. If the temperature is too high, by-products are easily produced and the reaction rate is difficult to control. Besides, such high temperature will hasten the deteriorating rate of the resin. If the temperature is too low, in addition to poor efficiency, the properties of the resulted resin product cannot meet the requirement for high temperature usage.

The flame retarding resin composition produced in accordance with the present invention can improve both the flame retarding properties and heat resistance of an epoxy resin without adding other processing assisting agents and flame retarding additives.

EXAMPLES

The present invention will be further described with reference to the following Examples, but the scope of the present invention is by no means limited.

The components used in the Synthesis Examples and Working Examples are described as follows:

Epoxy resin 1 is a diglycidyl ether of bisphenol A, sold under trade name BE188EL and manufactured by Chang Chun Plastics Co., Ltd., Taiwan. The epoxy equivalent weight is in the range of 185 to 195 g/eq, the hydrolytic chlorine is under 200 ppm, and the viscosity thereof is in the range of 11,000 to 15,000 cps/25° C.

Epoxy resin 2 is a polyglycidyl ether of cresol phenolic condensate, sold under trade name CNE200ELD and manufactured by Chang Chun Plastics Co., Ltd., Taiwan. The epoxy equivalent weight is in the range of 190 to 210 g/eq.

Epoxy resin 3 is a phenolic polyglycidyl ether, sold under trade name PNE177 and manufactured by Chang Chun Plastics Co., Ltd., Taiwan. The epoxy equivalent weight is in the range of 170 to 190 g/eq.

Epoxy resin 4 is a diglycidyl ether of tetrabromobisphenol A, sold under trade name BEB530A80 and manufactured by Chang Chun Plastics Co., Ltd., Taiwan. The epoxy equivalent weight is m the range of 430 to 450 g/eq and bromine content is in the range of 18.5 to 20.5 weight %.

Epoxy resin 5 is sold under trade name BE501 and manufactured by Chang Chun Plastics Co., Ltd., Taiwan. The epoxy equivalent weight is in the range of 490 to 510 g/eq.

Hardener A is a solution of 10% dicyanodiamide in DMF.

Hardener B is a phosphorus- and nitrogen-containing resin hardener of the present invention with the following formula:

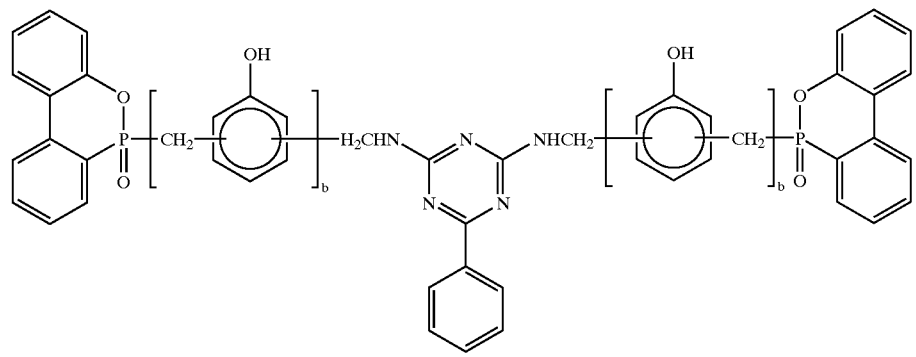

wherein b is an integer of from 0 to 20.

Hardening promoter A is a solution of 10% 2-methylimidazole (2MI) in methyl ethyl ketone.

The epoxy equivalent weight, the viscosity of a varnish, and the solid content used herein are measured by the following methods:

(1) Epoxy equivalent weight (EEW): the epoxy resin is dissolved in a mixed solvent (chlorobenzene: chloroform= 1:1), then the mixture is titrated with HBr/glacial acetic acid. EEW is determined according to the method in ASTM D1652. The indicator used is crystal violet.

(2) Viscosity: A varnish sample of the phosphorus-containing epoxy resin is placed into a thermostated trough at 25° C. for 4 hours, and the viscosity is measured by a Brookfield viscosimeter at 25° C.

(3) Solid content: After baking a varnish sample containing the phosphorus-containing epoxy resin of the present invention at 150° C. for 60 minutes, non-volatiles in weight % are determined, which is the solid content.

Synthesis Example 1

Synthesis of Phosphorus-and Nitrogen-containing Resin Hardener (hardener B).

Phenol (1410 g, 15 mole), 92% polyformaldehyde (244.7 g, 7.5 mole), benzoguanamine (337 g, 1.8 mole), 9,10-dihydro-9-oxa-10-phosphoanthracene-10-oxide (HCA) (259 g, 1.2 mole) and oxalic acid (11.2 g) were placed into a 3-liter, 5-necked glass reactor equipped with an electric heating mantle, a temperature controller, an electric stirrer with a stirring rod, a nitrogen gas inlet, a thermal couple, a water-cooled condenser and a feeding funnel. After being melted, the mixture was vacuum dried. Then, nitrogen gas was bubbled into the mixture. This process of vacuum drying and nitrogen gas bubbling was repeated twice. The temperature was raised to the range of 100° C. to 110° C., and the reaction was carried out for 3 hours. Further, the temperature was raised to the range of 120° C. to 125° C., and the reaction was carried out for 2 hours. After the reaction was completed, the un-reacted phenol and the water of condensation reaction were distilled off under normal pressure. The obtained product, the phosphorus-and nitrogen-containing resin hardener hardener B) of the present invention, was kept under vacuum, at 180° C., for 1 hour. After analysis, the softening point thereof was 161° C., theoretical nitrogen content was 10.0 weight %, phosphorus content was 2.93 weight % and the equivalent weight of active hydrogen was 210 g/eq.

Working Examples 1 to 6 and Comparative Example 1

In a vessel equipped with a stirrer and a condenser, hardener B obtained in Synthesis Example 1, an other hardener, epoxy resin, hardening promoter and solvents were formulated according to the addition ratios given in Table 1 into epoxy resin varnishes.

TABLE 1

| Composition Formula (g) | Working Example 1 | Working Example 2 | Working Example 3 | Working Example 4 | Working Example 5 | Working Example 6 | Comparative Example 1 |
|---|---|---|---|---|---|---|---|
| Epoxy Resin 1 | 146 | | 146 | | | | |
| Epoxy Resin 2 | 533 | 580 | | | | | |
| Epoxy Resin 3 | | | 555 | 555 | 500 | | |
| Epoxy Resin 4 | | | | | | | 1250 |
| Epoxy Resin 5 | | 130 | | 412 | | 1905 | |
| Hardener A | | | | | | | 265 |
| Hardener B | 700 | 700 | 700 | 800 | 475 | 800 | |
| Hardener C | | | | | 59 | | |
| Hardening Promoter A | 1.5 | 1.5 | 1.5 | 2.1 | 2.3 | 2.2 | 6.25 |
| Acetone | 530 | 530 | 530 | 580 | 380 | 994 | 158 |
| Propylene Glycol Monomethyl Ether | 403 | 403 | 403 | 598 | 300 | 800 | |

A glass-fiber fabric was impregnated in the formulated epoxy resin varnishes, then dried at 180° C. for 120 minutes, so that prepregs were formed. The glass transition temperatures thereof were measured by DSC (differential scanning calorimeter, TA2910), wherein the temperature range was 50° C. to 250° C. and the temperature raising rate was 20° C./min. The flame retardant properties thereof were measured by the flame test m accordance with the method of UL746. The samples of prepregs were cut into 5 pieces of 12.5 mm×1.3 mm in size. Each piece was burned 2 times. The flame test was passed when no more than 50 seconds in total was taken in ten burnings and no more than 10 seconds was taken in a single burning. The results are shown in Table 2.

TABLE 2

| | Working Example 1 | Working Example 2 | Working Example 3 | Working Example 4 | Working Example 5 | Working Example 6 | Comparative Example 1 |
|---|---|---|---|---|---|---|---|
| Flame Test | Pass | Pass | Pass | Pass | Pass | Pass | Pass |
| Tg (I) ° C. | 163 | 160 | 151 | 148 | 158 | 144 | 132 |

Eight pieces of the prepregs were piled up. A sheet of 35 μm copper foil was placed on its top and bottom sides, which were laminated at 185° C., under a pressure of 25 kg/cm$^2$, and formed into laminated entities of epoxy resin and glass-fiber fabric. The results of physical properties analysis are given in Table 3.

TABLE 3

| Test Item | Condition and Spec. | Working Example 3 | Working Example 4 | Comparative Example 1 |
|---|---|---|---|---|
| Solder Resistance | 288° C. Spec. > 300 sec | Pass | Pass | Fail |
| Peeling Strength | Spec. > 8 lb/in | 8.92 | 8.56 | 9.25 |
| Surface Resistance | Spec. > $10^{12}$ | $2.5 \times 10^{15}$ | $3.3 \times 10^{15}$ | $2.9 \times 10^{15}$ |
| Volume Resistance | Spec. > $10^{10}$ | $11 \times 10^{13}$ | $2.0 \times 10^{13}$ | $1.2 \times 10^{14}$ |
| Dielectric Constant | Spec. < 4.3 | 4.45 | 4.81 | 4.72 |
| Dissipation Factor | — | 0.021 | 0.023 | 0.022 |

Working Examples 7 to 10 and Comparative Example 2

In a vessel equipped with a stirrer and a condenser, epoxy resin varnishes were prepared according to the addition ratios given in Table 4.

TABLE 4

| Composition Formula (g) | Working Example 7 | Working Example 8 | Working Example 9 | Working Example 10 | Comparative Example 2 |
|---|---|---|---|---|---|
| Epoxy Resin 1 | 12 | 6 | | | |
| Epoxy Resin 2 | 50 | 45 | | 45 | |
| Epoxy Resin 3 | | | 40 | | |
| Epoxy Resin 4 | | | | | 125 |
| Epoxy Resin 5 | | 23 | 20 | 20 | |
| Hardener A | | | | | 26.5 |
| Hardener B | 62.6 | 44.5 | 47.8 | 52.9 | |
| Hardener C | | 9.54 | 5.31 | | |
| Hardening Promoter A | 0.21 | 0.22 | 0.35 | 0.36 | 0.65 |
| Propylene Glycol Monomethyl Ether | 21 | 21 | 17.7 | 19.3 | |
| Acetone | 20 | 21 | 20 | 20 | |

The epoxy resin compositions obtained from the above Working Examples 7, 8 and 10 and Comparative Examples 2 were coated with a thick coating of 80 µm on the rough surface of a sheet of 18 µm copper foil, and dried at 150° C. The obtained epoxy resin-coated copper foils were placed on the top and bottom sides of the prepreg made from the epoxy resin composition of Working Example 1, which were laminated at 185° C., under a pressure of 25 kg/cm², and formed into multi-layered boards. The results of physical properties tests of the multi-layered boards are given in Table 5.

TABLE 5

| Test Item | Condition and Spec. | Working Example 7 | Working Example 8 | Working Example 10 | Comparative Example 2 |
|---|---|---|---|---|---|
| Flame Test | UL94V-0 | Pass | Pass | Pass | Pass |
| Solder Resistance | 288° C. Spec. > 300 sec | Pass | Pass | Pass | Fail |
| Peeling Strength | IPC Spec. > 6 lb/in (18 µm) | 7.3 | 7.9 | 8.1 | 8.4 |

As is known from the above, compared to hardeners not containing phosphorus and nitrogen, the phosphorus- and nitrogen-containing resin hardener of the present invention exhibits superior flame retarding properties and solder resistance, while the peeling strength thereof is not decreased.

What is claimed is:
1. A phosphorus- and nitrogen-containing resin hardener, which has a structure represented by the following formula:

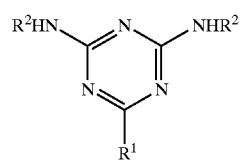

wherein R² represents a group represented by the following formula:

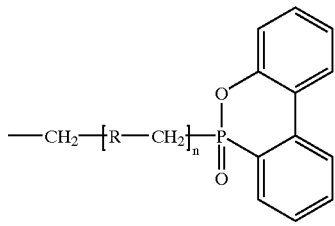

wherein n is an integer of from 0 to 20, and
R represents phenylene, naphthylene or a group represented by the following formula:

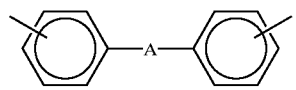

wherein A represents —O—, —S—, —SO₂—, —CO—, —CH₂—, —C(CH₃)₂— or a group represented by the following formula:

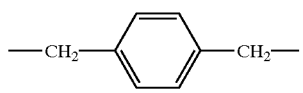

and R¹ represents NHR², C₁₋₆alkyl or phenyl;
in the above groups represented by R and A, the aromatic group may be substituted by one or more substituents selected from the group consisting of hydroxy, amino, carboxy and C₁₋₆alkyl.

2. A phosphorus- and nitrogen-containing resin hardener, which is a compound of the following formula:

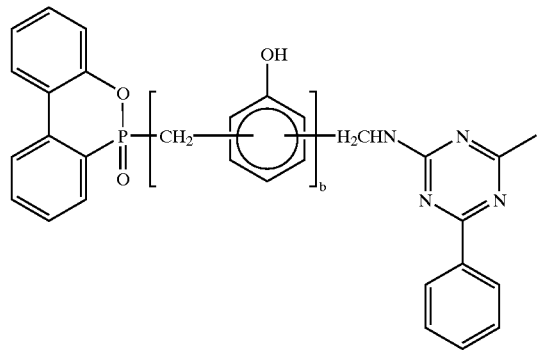

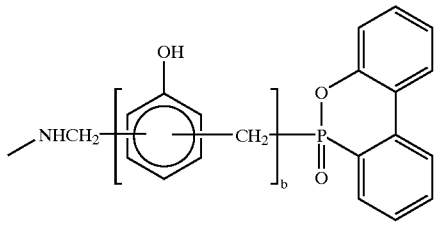

wherein b is an integer of from 0 to 20.

3. A flame retarding resin composition, which comprises (A) an epoxy resin, (B) the phosphorus- and nitrogen-containing resin hardener according to claim 1 or 2, and (C) a hardening promoter.

4. The flame retarding resin composition according to claim 3, wherein said epoxy resin is selected from the group consisting of glycidyl ethers of bisphenols, glycidyl ethers of biphenols, glycidyl ethers of dihydroxybenzenes, glycidyl ethers of nitrogen-containing hereto rings, glycidyl ethers of dihydroxynaphthalene, polyglycidyl ethers of phenolics and polyglycidyl ethers of polyhydric phenols.

5. The flame retarding resin composition according to claim 3, wherein said hardening promoter is selected from the group consisting of tertiary amines, tertiary phosphines, quaternary ammonium salts, quaternary phosphonium salts, boric trifluoride complexes, lithium compounds and imidazole compounds.

6. The flame retarding resin composition according to claim 3, wherein the amount of the component (B) hardener is 20 to 140% of the equivalent weight of the reactive hydrogen in said hardener, when the epoxy equivalent weight of the component (A) epoxy resin is taken as 100%.

7. The flame retarding resin composition according to claim 3, wherein the amount of the component (C) hardening promoter is from 50 to 50,000 ppm based on the total weight of said flame retarding resin composition.

8. The flame retarding resin composition according to claim 3, which further comprises other hardeners selected from the group consisting of amines, bisphenolic resin, dihydroxybenzenes, polyhydric phenolic resin and phenolics.

9. A prepreg made of a flame retarding resin composition according to claim 3.

10. A composite made of a flame retarding resin composition according to claim 3.

11. A laminate made of a flame retarding resin composition according to claim 3.

12. A printed circuit board made of a flame retarding resin composition according to claim 3.

13. The flame retarding resin composition according to claim 3, wherein the composition is a substrate for build-up of resin coated copper.

14. The flame retarding resin composition according to claim 3, wherein the composition is an epoxy molding compound.

* * * * *